(12) United States Patent
Pavliv

(10) Patent No.: US 6,727,286 B2
(45) Date of Patent: Apr. 27, 2004

(54) PHARMACEUTICAL COMPOSITION OF 2-(4-ISOBUTYLPHENYL) PROPIONIC ACID

(75) Inventor: Leo Pavliv, Morrisville, NC (US)

(73) Assignee: Cumberland Pharmaceuticals Inc., Nashville, TX (US)

( * ) Notice: Subject to any disclaimer, the term of this patent is extended or adjusted under 35 U.S.C. 154(b) by 42 days.

(21) Appl. No.: 09/985,246

(22) Filed: Nov. 2, 2001

(65) Prior Publication Data

US 2003/0100612 A1 May 29, 2003

(51) Int. Cl.$^7$ ............................................. A61K 31/195
(52) U.S. Cl. ........................ 514/565; 514/568; 514/57
(58) Field of Search ............................... 514/565, 568, 514/57

(56) References Cited

U.S. PATENT DOCUMENTS

| | | | |
|---|---|---|---|
| 4,279,926 A | 7/1981 | Bruzzese et al. | 424/316 |
| 4,593,044 A | 6/1986 | Metz | 514/557 |
| 4,687,781 A | 8/1987 | Ehrenpreis et al. | 514/557 |
| 4,748,174 A | 5/1988 | Veronesi | 514/226.5 |
| 4,834,966 A | 5/1989 | Gazzaniga et al. | 424/43 |
| 5,019,563 A | 5/1991 | Hunter et al. | 514/58 |
| 5,028,625 A | 7/1991 | Motola et al. | 514/557 |
| 5,200,558 A | 4/1993 | Kwan | 562/496 |
| 5,324,749 A | 6/1994 | Woog et al. | 514/562 |
| 5,463,117 A | 10/1995 | Stroppolo et al. | 562/496 |
| 5,500,226 A | 3/1996 | Stroppolo et al. | 424/466 |
| 5,510,385 A | 4/1996 | Stroppolo et al. | 514/555 |
| 5,519,057 A | 5/1996 | Loew et al. | 514/568 |
| 5,645,857 A | 7/1997 | Stroppolo et al. | 424/464 |
| 5,693,312 A | 12/1997 | Stroppolo et al. | 424/44 |
| 6,005,005 A | 12/1999 | Stroppolo et al. | 514/565 |

FOREIGN PATENT DOCUMENTS

| | | |
|---|---|---|
| JP | 63093718 A | 4/1988 |
| WO | 91/15202 | 10/1991 |

OTHER PUBLICATIONS

Carter et al, Chemotherapy of Cancer, 1981, Appendix C pp. 361–367.*

Van Overmeire, B., et al., "A Comparison of Ibuprofen and Indomethacin for Closure of Patent Ductus Arteriosus," *The New England Journal of Medicine* 343:674–681 (2000).

Dormond, O., et al., "Inhibition of Tumor Angiogenesis by Non–Steroidal Anti–Inflammatory Drugs: Emerging Mechanisms and Therapeutic Perspectives," *Drug Resistance Updates*, 4:314–321 (2001).

Elmore, E., et al., "Comparative Tissue–Specific Toxicities of 20 Cancer Preventive Agents Using Cultured Cells From 8 Different Normal Human Epithelia," *In Vitro & Molecular Toxicology* 14:191–207 (2001).

Wargovich, M.J., et al., "Inhibition of Aberrant Crypt Growth by Non–Steroidal Anti–Inflammatory Agenty and Differentiation Agents in the Rat Colon," *Int. J. Cancer*, 60:515–519 (1995).

Asea, A., et al., "Cyclooxygenase Inhibitors are Potent Sensitizers of Prostate Tumors to Hyperthermia and Radiation," *Int. J. Hyperthermia*, 17:401–414 (2001).

Eberlein, T.J., et al., "Ibuprofen Causes Reduced Toxic Effects of Interleukin 2 Administration in Patients with Metastatic Cancer," *Arch. Surg.*, 124:542–547 (1989).

Uotila, P., et al., "Increased Expression of Cyclooxygenase–2 and Nitric Oxide Synthase–2 in Human Prostate Cancer," *Urol. Res.*, 29:25–28 (2001).

Dang, C.T., et al., "Potential Role of Selective COX–2 Inhibitors in Cancer Management," *Oncology*, 16:30–36 (2002).

Maitra, A., et al., "Cyclooxygenase 2 Expression in Pancreatic Adenocarcinoma and pancreatic Intraepithelial Neoplasia," *Anatomic Pathology*, 118:194–201 (2002).

An, K.P., et al., "Cyclooxygenase–2 Express in Murine and Human Nonmelanoma Skin Cancers: Implications for Therapeutic Approaches," *Photochemistry and Photobiology*, 76:73–80 (2002).

McEntee, M.F., et al. "Cyclooxygenase–2 Expression in Spontaneous Intestinal Neoplasia of Domestic Dogs," *Vet. Pathol.*, 29:428–436 (2002).

Lin, SK., et al., "Sequential Expressions of MMP–1, TIMP–1, IL–6, and COX–2 Genes in Induced Periapical Lesions in Rats," *Eur. J. Oral. Sci.*, 110:246–253 (2002).

Koki, A.T., et al., "Characterization of Cyclooxygenase–2 (COX–2) during Tumorigenesis in Human Epithelial Cancers: Evidence for Potential Clinical Utility of COX–2 Inhibitors in Epithelial Cancers," *Prostaglandins, Leukotrienes and Essential Fatty Acids*, 66:13–18 (2002).

Kawamoto, T., et al., "Expression of Cyclooxygenase–2 in the Subserosal Layer Correlates with Postsurgical Prognosis of Pathological Tumor Stage 2 Carcinoma of the Gallbladder," *Int. J. Cancer*, 98:427–434 (2002).

Jaeckel, E.C., et al., "Correlation of Expression of Cyclooxygenase–2, Vascular Endothelial Growth Factor, and Peroxisome Proliferator–Activated Receptor δ With Head and Neck Squamous Cell Cancinoma," *Arch. Otolaryngol. Head Surg.*, 127:1253–1259 (2001).

Poon, R., et al., "Cyclooxygenase–Two (COX–2) Modulates Proliferation in Aggressive Fibromatosis (Desmoid Tumor)," *Oncogene*, 20:451–460 (2001).

* cited by examiner

*Primary Examiner*—Rebecca Cook
(74) *Attorney, Agent, or Firm*—Finnegan, Henderson, Farabow, Garrett & Dunner, L.L.P.

(57) ABSTRACT

The present invention provides a pharmaceutical composition comprising an aqueous solution of arginine and ibuprofen, wherein the molar ratio of arginine to ibuprofen is less than 1:1, as well as a method of making the same. The present invention also provides a method of treating a condition chosen from pain, inflammation, fever, and/or other conditions alleviated by ibuprofen comprising administering a pharmaceutical composition comprising an aqueous solution of arginine and ibuprofen, wherein the molar ratio of arginine to ibuprofen is less than 1:1.

44 Claims, 1 Drawing Sheet

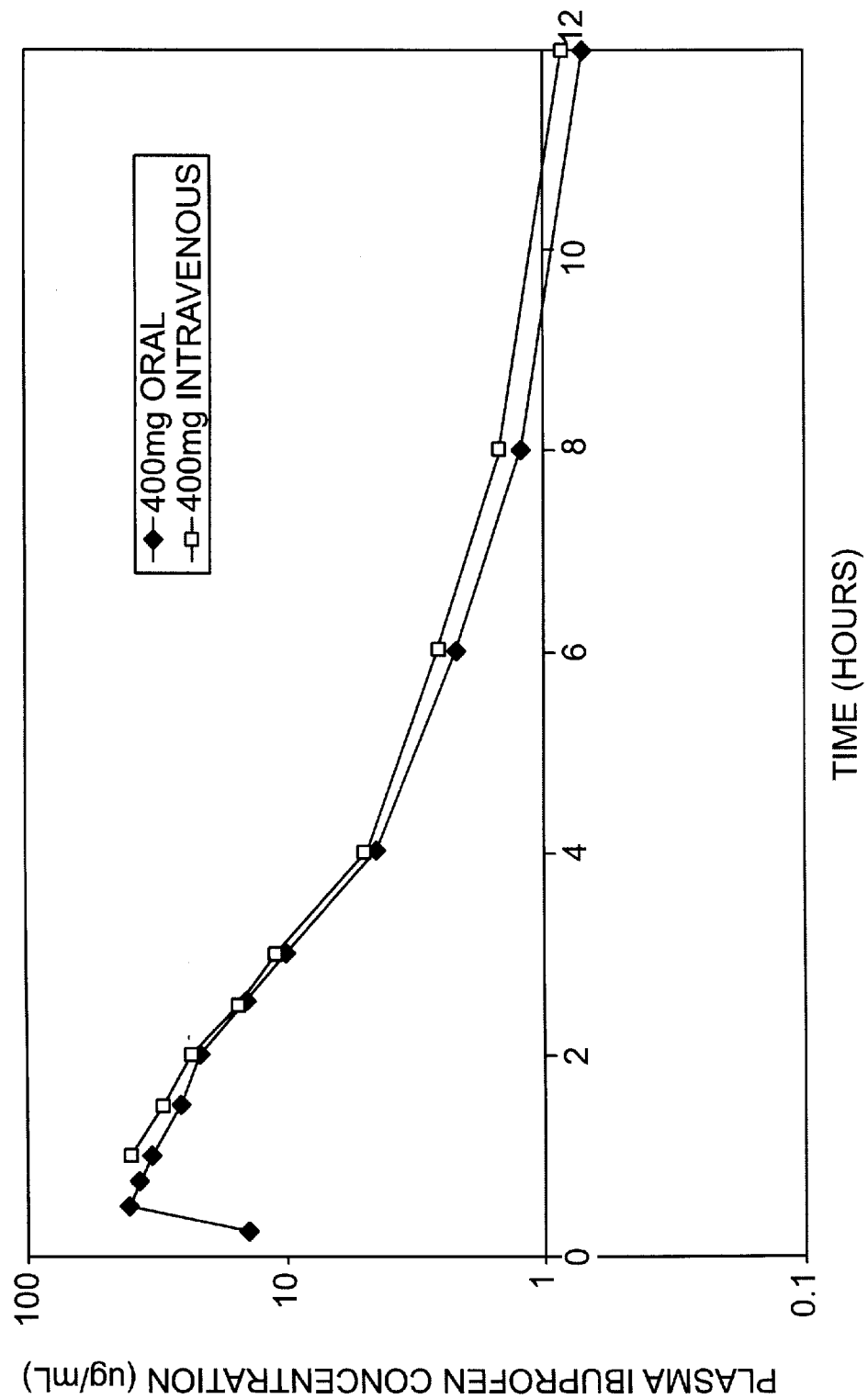

PHARMACEUTICAL COMPOSITION OF 2-(4-ISOBUTYLPHENYL) PROPIONIC ACID

The present invention relates to a pharmaceutical composition for oral or injectable (parenteral) use containing 2-(4-isobutylphenyl) propionic acid and a basic amino acid, and more particularly, where the amino acid is arginine.

BACKGROUND OF INVENTION 2-(4-isobutylphenyl) propionic acid, whose International Nonproprietary Name is ibuprofen, is a well-known anti-inflammatory drug having a molecular weight of 206.28 and the following chemical structure:

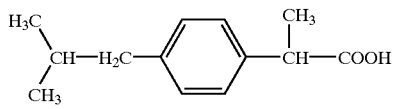

(Merck Index 12th ed., n4925, page 839). Originally patented in the 1960's, ibuprofen is now marketed generically, as well as under the tradenames of Motrin®, Advil®, and Nuprin® for the treatment of pain, inflammation, and fever.

Ibuprofen is readily available as the racemic mixture ((RS)-Ibuprofen) of the two enantiomers, (R)-Ibuprofen and (S)-Ibuprofen. Even though the (S) enantiomer is the biologically active form, most preparations contain the racemic mixture since the (R) enantiomer is converted to the active (S) form in-vivo. For simplicity, hereinafter the term "ibuprofen" will be used to indicate any one of the (R) enantiomer, the (S) enantiomer, or the racemate.

Many amino acids, including arginine, are available as both the D and L forms. For simplicity, hereinafter the term "arginine" will indicate the D or L form of arginine or a mixture of (D)-arginine and (L)-arginine. Arginine has a molecular weight of 174.20.

Although ibuprofen has many advantages over other analgesics such as aspirin and acetaminophen, it is very poorly soluble in water. Thus, certain dosage forms of ibuprofen, especially oral or injectable liquids, have been difficult to develop. Several U.S. patents have addressed this problem.

For example, U.S. Pat. No. 4,309,421 appears to describe water-soluble complexes of ibuprofen and phospholipids suitable for parenteral administration. U.S. Pat. Nos. 4,859,704 and 4,861,797 appear to describe the synthesis of alkali metal salts of ibuprofen for preparing a liquid ibuprofen formulation.

Other U.S. patents appear to address this problem by preparing an ibuprofen salt with a basic amino acid as the active pharmaceutical ingredient and then solubilizing the salt to produce a liquid dosage form.

For example, U.S. Pat. No. 5,200,558 appears to describe enhanced analgesic effects of S (+) ibuprofen as salts of L and D amino acids, including arginine, in various dosage forms, including as an injectable solution. U.S. Pat. No. 4,279,926 appears to describe the use of basic amino acid salts of propionic acids for relieving pain and treating inflammatory conditions. Similarly, U.S. Pat. No. 5,463,117 appears to describe the preparation of salts of ibuprofen with basic amino acids. Finally, U.S. Pat. No. 6,005,005 appears to describe a liquid composition for oral use containing ibuprofen and arginine.

However, the approaches described in the patents discussed above have, among others, the disadvantage of requiring the formation of a salt before solubilization, where the salt must be isolated and tested prior to producing the dosage form. Additionally, the ibuprofen formulations resulting from those processes have at least a 1:1 molar ratio of amino acid to ibuprofen. It is beneficial from both a cost and development point to not have to form a salt and isolate and test it prior to producing the dosage form. It is also beneficial in most cases to minimize the amount of non-active components, including salts, used in therapeutic products in order to minimize potential side effects. Furthermore, for injectable products it is beneficial to produce a liquid dosage form of ibuprofen having a pH similar to that of blood (pH 7.4). Finally, it is beneficial for an injectable and oral product to have similar pharmacokinetics to minimize the need for dosage adjustments.

SUMMARY OF THE INVENTION

The present invention utilizes arginine to solubilize ibuprofen during the manufacture of the pharmaceutical product instead of using a salt form of ibuprofen. Thus, an embodiment of the present invention is a pharmaceutical composition comprising an aqueous solution of arginine and ibuprofen, wherein the molar ratio of arginine to ibuprofen is less than 1:1. Another embodiment of the present invention is a method of making a pharmaceutical composition comprising an aqueous solution of arginine and ibuprofen, wherein the molar ratio of arginine to ibuprofen is less than 1:1. Still other embodiments of the present invention are directed to methods of treating pain, inflammation, fever, and/or other conditions alleviated by ibuprofen comprising administering a pharmaceutical composition comprising an aqueous solution of arginine and ibuprofen, wherein the molar ratio of arginine to ibuprofen is less than 1:1.

BRIEF DESCRIPTION OF THE FIGURE

The FIGURE shows plasma concentration-time curves for 400 mg oral and intravenous ibuprofen.

DETAILED DESCRIPTION OF THE INVENTION

The present inventor has discovered that a liquid composition of ibuprofen can be produced by combining ibuprofen with arginine at molar ratios that minimize the amount of arginine necessary to solubilize the ibuprofen. Thus, one embodiment of the present invention is a pharmaceutical composition comprising an aqueous solution of arginine and ibuprofen, wherein the molar ratio of arginine to ibuprofen is less than 1:1. In another embodiment of the invention, the molar ratio of arginine to ibuprofen is from about 0.10:1 to about 0.999:1. In yet other embodiments of the invention, the molar ratio of arginine to ibuprofen is 0.92:1 or 0.60:1 or 0.99:1.

The present inventor has further discovered a method of making a pharmaceutical composition comprising an aqueous solution of arginine and ibuprofen in a molar ratio of less than 1:1, wherein the method comprises the following: adding arginine to water, mixing until the arginine is dissolved to form an arginine solution, adding ibuprofen to the arginine solution, and mixing until the ibuprofen is dissolved to form the aqueous solution of arginine and ibuprofen, optionally adding sufficient water to result in the desired concentration of ibuprofen, and optionally separating any precipitate using standard methods such as filtration or centrifugation. The resulting product is a clear, colorless solution that can readily be passed through a 0.2 micron filter. The pH of the resulting solution can be adjusted using techniques known in the art to achieve a desired pH, for example a pH similar to that of blood. Finally, the resulting solution can be terminally sterilized or lyophilized.

The present inventor has further discovered a method of treating a condition chosen from pain, inflammation, fever, and/or other conditions alleviated by ibuprofen comprising administering to a patient in need thereof an effective amount of a pharmaceutical composition comprising an aqueous solution of arginine and ibuprofen, wherein the molar ratio of arginine to ibuprofen is less than 1:1. Other conditions alleviated by ibuprofen include, but are not limited to, patent ductus arteriosis and certain forms of cancer. The pharmaceutical composition may be administered by injection (intravenous or intramuscular) or orally. Dosages of the pharmaceutical composition range from about 5 to about 1000 mg of ibuprofen in the pharmaceutical composition and can be determined by one of ordinary skill in the art. In one embodiment, the dosage is from about 100 to about 800 mg of ibuprofen in the pharmaceutical composition. In a further embodiment, the dosage is about 400 mg of ibuprofen in the pharmaceutical composition. In still another embodiment, the dosage of the pharmaceutical composition is from about 5 to about 10 mg/kg, and in a further embodiment the dosage of the pharmaceutical composition is about 7.5 mg/kg.

The following examples represent specific embodiments of the foregoing discovery, and they are not representative of the entire scope of the invention. The ibuprofen and arginine used in the examples are United States Pharmacopoea grade, but other pharmaceutically acceptable materials can be utilized.

EXAMPLE 1

Add 8.2 kg of arginine to approximately 80 liters of water for injection and mix until dissolved. Add 10.0 kg of ibuprofen to the arginine solution and mix until dissolved. Add a sufficient quantity of water to equal 100 liters, resulting in a 100 mg/mL solution having a molar ratio of 0.97:1 (arginine:ibuprofen). The product results in a clear, colorless, solution that can readily be passed through a 0.2 micron filter. The pH of the resulting solution is approximately 7.4 and can be adjusted to achieve somewhat lower or higher pH's as desired. The solution can further be terminally sterilized to minimize the likelihood of a non-sterile product.

EXAMPLE 2

Lower concentrations of ibuprofen can be prepared by using lesser amounts of arginine and ibuprofen. Add 41 g of arginine to approximately 80 liters of water for injection and mix until dissolved. Add 50 g of ibuprofen to the arginine solution and mix until dissolved. Add a sufficient quantity of water to equal 100 liters, resulting in a 0.5 mg/mL solution having a molar ratio of 0.97:1 (arginine:ibuprofen). The product results in a clear, colorless, solution that can readily be passed through a 0.2 micron filter. The pH of the resulting solution can be adjusted to achieve a desirable pH.

EXAMPLE 3

Lower concentrations of arginine can be used to prepare the ibuprofen solution. Add 3.8 kg of arginine to approximately 80 liters of water for injection and mix until dissolved. Add 7.5 kg of ibuprofen to the arginine solution and mix until dissolved. Add a sufficient quantity of water to equal 100 liters, resulting in a 75 mg/mL solution having a molar ratio of 0.60:1 (arginine:ibuprofen). The product can be passed through a 0.2 micron filter resulting in a clear colorless solution. The pH of the resulting solution can be adjusted to achieve a desirable pH.

EXAMPLE 4

Higher concentrations of arginine can be used to prepare the ibuprofen solution. Add 8.43 g of arginine to 80 mL of water for injection and mix until dissolved. Add 10 g of ibuprofen to the arginine solution and mix until dissolved. Add a sufficient quantity of water to equal 100 mL, resulting in a 100 mg/mL solution having a molar ratio of 0.99:1 (arginine:ibuprofen). The product results in a clear, colorless, solution that can readily be passed through a 0.2 micron filter. The pH of the resulting solution can be adjusted to achieve a desirable pH.

EXAMPLE 5

4.384 kg of arginine were added to approximately 45 liters of water for injection and mixed until dissolved. 5.62 kg of ibuprofen were added to the arginine solution and mixed until dissolved. The pH of the resulting solution was approximately 7.4, but could be adjusted to achieve somewhat lower or higher pH's as desired. A sufficient quantity of water was added to the resulting solution to equal 56.2 liters, resulting in a 100 mg/mL solution having a molar ratio of 0.92:1 (arginine:ibuprofen). The product resulted in a clear, colorless solution that could readily be passed through a 0.2 micron filter. The solution was terminally sterilized to assure that the product was sterilized.

EXAMPLE 6

In an attempt to demonstrate similar pharmacokinetics between a 60 minute infusion of intravenous ibuprofen solubilized with arginine as in Example 5 and oral ibuprofen (in the form of Advil® Liqui-Gels®), volunteers received single oral or intravenous doses (200 mg, 400 mg, or 800 mg) of either oral or intravenous ibuprofen product. Blood samples were collected at specified times relative to the start of dosing, and plasma ibuprofen concentrations were measured. The following pharmacokinetic parameters were calculated: $C_{max}$ (maximum concentration), $AUC_{0-12}$ (area under the curve from initial time to 12 hours), $AUC_{0-\infty}$, (area under the curve from initial time to infinity), $T_{max}$ (time of maximum concentration), $k_{el}$ (elimination constant), and $t_{1/2}$ (half life). Statistical analyses were performed on the plasma concentration data and pharmacokinetic parameters were calculated for the 12 patients on each of the three doses examined.

The plasma concentration-time profiles for both oral and intravenous administration of ibuprofen were observed to be very similar. The concentration-time data for the 400-mg oral and intravenous doses are shown in the Figure to illustrate this result. On the basis of the ibuprofen concentration-time data, the following pharmacokinetic parameters were calculated (Table 1).

TABLE 1

Pharmacokinetic Parameters After Oral and Intravenous Administration of Ibuprofen

| Parameter | Cohort 1: 200 mg | | Cohort 2: 400 mg | | Cohort 3: 800 mg | |
|---|---|---|---|---|---|---|
| | Oral | Intravenous | Oral | Intravenous | Oral | Intravenous |
| $C_{max}$ (µg/mL) | 24.7 ± 4.2 | 19.3 ± 3.1 | 42.9 ± 4.9 | 39.2 ± 6.1 | 81.0 ± 18.8 | 72.6 ± 9.6 |
| $AUC_{0-12}$ (µg · hr/mL) | 67.9 ± 16.9 | 63.2 ± 12.5 | 108.0 ± 23.9 | 108.5 ± 29.0 | 211.0 ± 47.6 | 192.2 ± 35.9 |
| $AUC_{0-\infty}$ (µg · hr/mL) | 69.9 ± 18.0 | 65.5 ± 14.1 | 110.8 ± 26.8 | 112.3 ± 32.8 | 218.4 ± 55.0 | 197.8 ± 39.9 |
| $T_{max}$ (hr) | 0.6 ± 0.2 | 1.1 ± 0.2 | 0.6 ± 0.1 | 1.1 ± 0.2 | 0.9 ± 0.5 | 1.0 ± 0.0 |
| $k_{el}$ (hr$^{-1}$) | 0.3 ± 0.0 | 0.3 ± 0.0 | 0.3 ± 0.1 | 0.3 ± 0.1 | 0.3 ± 0.1 | 0.3 ± 0.0 |
| $t_{½}$ (hr) | 2.4 ± 0.2 | 2.3 ± 0.2 | 2.2 ± 0.5 | 2.2 ± 0.5 | 2.3 ± 0.5 | 2.3 ± 0.4 |

Data shown are mean ± standard deviation.

The linearity of ibuprofen pharmacokinetics after oral and intravenous administration was analyzed. The results indicated that for both intravenous ibuprofen and oral ibuprofen, $AUC_{0-12}$, $AUC_{0-\infty}$, and $C_{max}$ increased in an appropriately linear manner with dose.

I claim:

1. A pharmaceutical composition comprising an aqueous solution of arginine and ibuprofen, wherein the molar ratio of arginine to ibuprofen is less than or equal to 0.97:1.

2. The pharmaceutical composition of claim 1, wherein the aqueous solution of arginine and ibuprofen has been terminally sterilized.

3. The pharmaceutical composition of claim 1, wherein the aqueous solution of arginine and ibuprofen has been lyophilized.

4. The pharmaceutical composition of claim 1, wherein the ibuprofen is (RS)-Ibuprofen.

5. The pharmaceutical composition of claim 1, wherein the ibuprofen is (S)-Ibuprofen.

6. The pharmaceutical composition of claim 1, wherein the arginine is L-arginine.

7. The pharmaceutical composition of claim 1, wherein the arginine is D-arginine.

8. The pharmaceutical composition of claim 1, wherein the molar ratio of arginine to ibuprofen is from about 0.10:1 to about 0.97:1.

9. The pharmaceutical composition of claim 8, wherein the molar ratio of arginine to ibuprofen is 0.92:1.

10. The pharmaceutical composition of claim 8, wherein the molar ratio of arginine to ibuprofen is 0.60:1.

11. The pharmaceutical composition of claim 8, wherein the molar ratio of arginine to ibuprofen is 0.97:1.

12. A method of making a pharmaceutical composition comprising an aqueous solution of arginine and ibuprofen, the method comprising dissolving arginine in water to form an arginine solution and dissolving ibuprofen in the arginine solution to form the aqueous solution of arginine and ibuprofen, wherein the molar ratio of arginine to ibuprofen is less than or equal to 0.97:1.

13. The method of claim 12, wherein the molar ratio of arginine to ibuprofen is from about 0.10:1 to about 0.97:1.

14. The method of claim 12, wherein the molar ratio of arginine to ibuprofen is 0.92:1.

15. The method of claim 12, wherein the molar ratio of arginine to ibuprofen is 0.60:1.

16. The method of claim 12, wherein the molar ratio of arginine to ibuprofen is 0.97:1.

17. The method of claim 12, further comprising terminally sterilizing the aqueous solution of arginine and ibuprofen.

18. The method of claim 12, further comprising lyophilizing the aqueous solution of arginine and ibuprofen.

19. The method of claim 12, wherein the ibuprofen is (RS)-Ibuprofen.

20. The method of claim 12, wherein the ibuprofen is (S)-Ibuprofen.

21. The method of claim 12, wherein the arginine is L-arginine.

22. The method of claim 12, wherein the arginine is D-arginine.

23. A method of treating one or more conditions chosen from pain, inflammation, fevers, and, patent ductus arteriosis comprising administering to a patient in need thereof an effective amount of an aqueous solution of arginine and ibuprofen, wherein the molar ratio of arginine to ibuprofen is less than or equal to 0.97:1.

24. The method of claim 23, wherein the molar ratio of arginine to ibuprofen is from about 0.10:1 to about 0.97:1.

25. The method of claim 23, wherein the molar ratio of arginine to ibuprofen is 0.92:1.

26. The method of claim 23, wherein the molar ratio of arginine to ibuprofen is 0.60:1.

27. The method of claim 23, wherein the molar ratio of arginine to ibuprofen is 0.97:1.

28. The method of claim 23, wherein the administration occurs via intravenous injection.

29. The method of claim 23, wherein the administration occurs via intramuscular injection.

30. The method of claim 23, wherein the administration occurs orally.

31. The method of claim 23, wherein the effective amount is from about 100 mg to about 800 mg of ibuprofen.

32. The method of claim 31, wherein the effective amount is about 400 mg of ibuprofen.

33. The method of claim 23, wherein the effective amount is about 7.5 mg/kg of ibuprofen.

34. The method of claim 23, wherein the condition is pain.

35. The method of claim 23, wherein the condition is inflammation.

36. The method of claim 23, wherein the condition is fever.

37. A pharmaceutical composition comprising an aqueous solution of arginine and ibuprofen prepared according to the method of claim 12.

38. The method of claim 23, wherein the condition is patent ductus arteriosis.

39. The pharmaceutical composition of claim 1, the molar ratio of arginine to ibuprofen is from about 0.60:1 to about 0.97:1.

40. The pharmaceutical composition of claim 39, wherein said molar ratio is from about 0.92:1 to about 0.97:1.

41. The method of claim 12, wherein the molar ratio of arginine to ibuprofen is from about 0.60:1 to about 0.97:1.

42. The method of claim 41, wherein the molar ratio of arginine to ibuprofen is from about 0.92:1 to about 0.97:1.

43. The method of claim 23, wherein the molar ratio of arginine to ibuprofen is from about 0.60:1 to about 0.97:1.

44. The method of claim 43, wherein the molar ratio of arginine to ibuprofen is from about 0.92:1 to about 0.97:1.

* * * * *

UNITED STATES PATENT AND TRADEMARK OFFICE
CERTIFICATE OF CORRECTION

PATENT NO. : 6,727,286 B2
DATED : April 27, 2004
INVENTOR(S) : Leo Pavliv

It is certified that error appears in the above-identified patent and that said Letters Patent is hereby corrected as shown below:

Title page,
Item [73], Assignee, "Nashville, TX" should read -- Nashville, TN --.
Item [*] Notice, "Subject to any disclaimer, ther term of this patent is extended or adjusted under 35 U.S.C. 154(b) by 42 days." should read -- Subject to any disclaimer, ther term of this patent is extended or adjusted under 35 U.S.C. 154(b) by 25 days. --.

Column 23,
Line 30, "fevers," should read -- fever, --.
Line 30, "and, patent" should read -- and patent --.
Line 65, "claim 1, the" should read -- claim 1, wherein the --.

Signed and Sealed this

Twenty-fifth Day of October, 2005

JON W. DUDAS
*Director of the United States Patent and Trademark Office*